(12) United States Patent
Poetsch et al.

(10) Patent No.: US 7,109,381 B2
(45) Date of Patent: Sep. 19, 2006

(54) ALDEHYDES CONTAINING A DIFLUOROOXYMETHYLENE BRIDGE

(75) Inventors: Eike Poetsch, Muehltal (DE); Werner Binder, Dieburg (DE); Volker Meyer, Gross-Zimmern (DE); Stephan Gürtler, Griesheim (DE); Juergen Eckstein, Rossdorf (DE); Michael Schwarz, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 63 days.

(21) Appl. No.: 10/854,676

(22) Filed: May 27, 2004

(65) Prior Publication Data

US 2004/0242905 A1    Dec. 2, 2004

(30) Foreign Application Priority Data

May 27, 2003   (DE)   ................. 103 24 313

(51) Int. Cl.
   *C07C 47/277*   (2006.01)
   *C07C 47/47*    (2006.01)
   *C07C 47/575*   (2006.01)
   *C07D 319/06*   (2006.01)

(52) U.S. Cl. ................. 568/442; 549/374; 549/373

(58) Field of Classification Search ............... 568/442; 549/374, 373
See application file for complete search history.

(56) References Cited

U.S. PATENT DOCUMENTS

| 5,997,766 | A  | 12/1999 | Kirsch et al. |
| 2003/0213935 | A1 | 11/2003 | Heckmeier et al. |
| 2003/0216554 | A1 | 11/2003 | Kirsch et al. |

FOREIGN PATENT DOCUMENTS

| DE | 102 17 771 | 10/2002 |
| DE | 102 29 476 | 2/2003 |
| DE | 102 43 776 | 4/2003 |
| EP | 1 416 030  | 5/2004 |

OTHER PUBLICATIONS

Iseki K et al.: "Catalytic Asymmetric Nitroaldol Reaction of Alpha. Alpha-Difluoro Aldehydes Mediated by Rare Earth-Lithium-Binol Complexes" Tetrahedron Letters, Elsevier Science Publishers, Amsterdam, NL, Bd. 37 Nr. 50 Dec. 9, 1996, pp. 9081-9084.

*Primary Examiner*—Kamal A. Saeed
*Assistant Examiner*—Jason M. Nolan
(74) *Attorney, Agent, or Firm*—Millen, White, Zelano, Branigan, P.C.

(57) ABSTRACT

Aldehydes containing a difluorooxymethylene bridge, of the general formula I

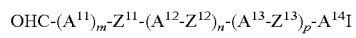

$$OHC-(A^{11})_m-Z^{11}-(A^{12}-Z^{12})_n-(A^{13}-Z^{13})_p-A^{14} \quad I$$

and the use and preparation thereof and the preparation of 1,3-dioxane compounds.

12 Claims, No Drawings

US 7,109,381 B2

ALDEHYDES CONTAINING A DIFLUOROOXYMETHYLENE BRIDGE

This application claims priority to Germany 103 24 313.5, filed on May 27, 2003, and is incorporated herein by reference in its entirety.

The invention, in one aspect, relates to aldehydes containing a difluorooxymethylene bridge, and to the use and preparation thereof, and to the preparation of 1,3-dioxane compounds.

Mesogenic compounds containing a difluorooxymethylene bridge ($CF_2O$ bridge) play an important role as constituents of liquid-crystalline mixtures for use, for example, in electro-optical display devices (see, for example, EP 844 229 A1 and EP 881 221 A1). However, their synthesis is often difficult, and for individual compounds the reaction parameters in the preparation processes usually have to be adapted in a specific and complex manner. Furthermore, the known preparation processes use linear synthetic routes, in which introduction of the $CF_2O$ group into the mesogenic molecule which has otherwise already been built up completely is only possible in one of the final steps of a frequently multistep synthesis, for example by conversion of an ester function in two steps (see EP 844 229 A1). These synthetic routes often prove to be inflexible and can only be applied to the synthesis of other molecules containing a difluorooxymethylene group within narrow limits. This applies in particular to molecules containing a $CF_2O$ bridge which have structural units—for example cyclic or acyclic acetal structures—which are sensitive, for example, to Lewis or protonic acids.

By contrast, successful strategies for the convergent synthesis of complex mesogenic compounds containing a —$CF_2O$— group from precursors (synthones) which are comparatively readily accessible and can be employed in a versatile manner are hitherto unknown, especially as there is a lack of such precursors in the literature.

An object of the present invention therefore is to provide precursors for the synthesis of compounds containing a difluorooxymethylene bridge.

This object is achieved by the aldehydes of the general formula I $$\text{OHC-}(A^{11})_m\text{-}Z^{11}\text{-}(A^{12}\text{-}Z^{12})_n\text{-}(A^{13}\text{-}Z^{13})_p\text{-}A^{14} \qquad \text{I}$$

where
$A^{11}$, $A^{12}$ and $A^{13}$, independently of one another, are

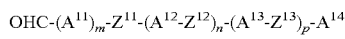

$A^{14}$ is

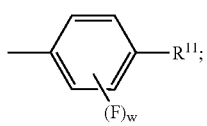

$Z^{11}$, $Z^{12}$ and $Z^{13}$, independently of one another, are a single bond, —$CH_2CH_2$—, —$CF_2CH_2$—, —$CH_2CF_2$—, —$CF_2CF_2$—, —CH=CH—, —C≡C—, —CO—O—, —O—CO—, —$CH_2O$—, —$OCH_2$— or —$CF_2O$—, where at least one of $Z^{11}$, $Z^{12}$ and $Z^{13}$ is —$CF_2O$—;
m, n and p, independently of one another, are 0 or 1;
q and w, independently of one another, are 0, 1, 2, 3 or 4;
$R^{11}$ is H, F, Cl, Br, I, CN, —NCS, an O-aralkyl radical, or an alkyl radical having from 1 to 15 carbon atoms which is unsubstituted or mono- or polysubstituted by F, Cl, Br, I and/or —CN, where one or more $CH_2$ groups in this radical may each, independently of one another, be replaced by —C≡C—, —CH=CH—, —O—, —S—, —CO—, —CO—O— or —O—CO— in such a way that hetero atoms are not linked directly to one another.

The aldehydes according to the invention have versatile usability for the synthesis of relatively complex compounds containing a difluorooxymethylene bridge. They are furthermore easily preparable and in high yield from comparatively simple starting compounds.

In connection with the present invention, the term "alkyl"—unless defined otherwise elsewhere in this description or in the claims—denotes a straight-chain or branched aliphatic hydrocarbon radical having from 1 to 15 (i.e. 1, 2, 3, 4, 5, 6, 7, 8, 9, 10, 11, 12, 13, 14 or 15) carbon atoms; this radical is unsubstituted or mono- or polysubstituted by identical or different fluorine, chlorine, bromine, iodine and/or cyano radicals.

If this alkyl radical is a saturated radical, it is also referred to as "alkanyl". Furthermore, the term "alkyl" also covers hydrocarbon radicals which are unsubstituted or correspondingly mono- or polysubstituted by identical or different F, Cl, Br, I and/or —CN radicals and in which one or more $CH_2$ groups may be replaced by —O— ("alkoxy", "oxaalkyl"), —S— ("thioalkyl"), —CH=CH— ("alkenyl"), —C≡C— ("alkynyl"), —CO—O— or —O—CO— in such a way that hetero atoms (O and S) are not linked directly to one another. Alkyl is preferably a straight-chain or branched, unsubstituted or substituted alkanyl, alkenyl or alkoxy radical having 1, 2, 3, 4, 5, 6, 7 or 8 carbon atoms. If alkyl is an alkanyl radical, this is preferably methyl, ethyl, n-propyl, i-propyl, n-butyl, i-butyl, t-butyl, n-pentyl, neopentyl, n-hexyl, n-heptyl, n-octyl; $CF_3$, $CHF_2$, $CH_2F$; $CF_2CF_3$. The alkanyl radical is particularly preferably straight-chain and unsubstituted or substituted by F.

Since one or more $CH_2$ groups in an alkyl radical in accordance with this invention may be replaced by —O—, the term "alkyl" also covers "alkoxy" or "oxaalkyl" radicals. Alkoxy is taken to mean an O-alkyl radical in which the oxygen atom is bonded directly to the group substituted by the alkoxy radical or to the substituted ring, and alkyl is as defined above; alkyl is preferably then alkanyl or alkenyl. Preferred alkoxy radicals are methoxy, ethoxy, propoxy, butoxy, pentoxy, hexoxy, heptoxy and octoxy, where each of these radicals may also be substituted, preferably by one or more fluorine atoms. Alkoxy is particularly preferably —$OCH_3$, —$OC_2H_5$, —O-n-$C_3H_7$, —O-n-$C_4H_9$, —O-t-$C_4H_9$, —$OCF_3$, —$OCHF_2$, —$OCH_2F$ or —$OCHFCHF_2$. In connection with the present invention, the term "oxaalkyl" denotes alkyl radicals in which at least one non-terminal $CH_2$ group has been replaced by —O— in such a way that no adjacent hetero atoms (O and S) are present. Oxaalkyl preferably covers straight-chain radicals of the formula $C_aH_{2a+1}$—O—$(CH_2)_b$—, where a and b are each, independently of one another, 1, 2, 3, 4, 5, 6, 7, 8, 9 or 10; a is particularly preferably an integer from 1 to 6, and b is 1 or 2.

If one or more CH$_2$ groups in an alkyl radical as defined above have been replaced by sulfur, a "thioalkyl" radical is present. "Thioalkyl" preferably covers a straight-chain radical of the formula —C$_a$H$_{2a+1}$—S—(CH$_2$)$_b$—, where a is 1, 2, 3, 4, 5, 6, 7, 8, 9 or 10, and b is 0, 1, 2, 3, 4, 5, 6, 7, 8, 9 or 10; a is particularly preferably an integer from 1 to 6, and b is 0, 1 or 2. The thioalkyl radical may likewise be substituted by F, Cl, Br, I and/or —CN and is preferably unsubstituted.

In connection with the present invention, the term "alkenyl" denotes an alkyl radical as defined above in which one or more —CH═CH— groups are present. If two —CH═CH— groups are present in the radical, this may also be referred to as "alkadienyl". An alkenyl radical may contain from 2 to 15 (i.e. 2, 3, 4, 5, 6, 7, 8, 9, 10, 11, 12, 13, 14 or 15) carbon atoms and is branched or preferably straight-chain. The radical is unsubstituted or mono- or poly-substituted by identical or different F, Cl, Br, I and/or CN radicals. Furthermore, one or more CH$_2$ groups may each, independently of one another, be replaced by —O—, —S—, —C≡C—, —CO—O— or —OC—O— in such a way that hetero atoms (O and S) are not bonded directly to one another. If the CH═CH group carries a radical other than hydrogen on the two carbon atoms, for example if it is a non-terminal group, the CH═CH group can exist in two configurations, namely as the E isomer and the Z isomer. In general, the E isomer (trans) is preferred. The alkenyl radical preferably contains 2, 3, 4, 5, 6 or 7 carbon atoms and is preferably vinyl, 1E-propenyl, 1E-butenyl, 1E-pentenyl, 1E-hexenyl, 1E-heptenyl, 2-propenyl, 2E-butenyl, 2E-pentenyl, 2E-hexenyl, 2E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl or 6-heptenyl. Particularly preferred alkenyl radicals are vinyl, 1E-propenyl and 3E-butenyl.

If one or more CH$_2$ groups in an alkyl radical have been replaced by —C≡C—, an alkynyl radical is present. Replacement of one or more CH$_2$ groups by —CO—O— or —O—CO— is also possible. The following radicals are preferred here: acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 2-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

In connection with the present invention, the term "O-aralkyl" represents an aryl-alkyl-O— radical, i.e. a radical in which an aryl substituent is linked to an atom, a chain, another radical or a functional group via an alkyl-oxygen bridge. The term aryl substituent here is taken to mean an aromatic hydrocarbon having from 6 to 18 carbon atoms which is optionally substituted by halogen, amino, nitro, alkanyl and/or alkoxy radicals, in particular a phenyl or naphthyl radical. The alkyl-oxygen bridge is preferably saturated. In particular, it is methylene-O (—CH$_2$—O—) or ethylene-O (—CH$_2$CH$_2$—O—). Preferred examples of an O-aralkyl radical are benzyl-O— and phenethyl-O—.

If radicals or substituents of the aldehydes according to the invention or the aldehydes according to the invention themselves can exist as optically active or stereoisomeric radicals, substituents or compounds since they contain, for example, a centre of asymmetry, these are also covered by the present invention. It is self-evident here that the aldehydes of the general formula I according to the invention can exist in isomerically pure form, for example as pure enantiomers, diastereomers, E or Z isomers, trans or cis isomers, or as a mixture of a plurality of isomers in any desired ratio, for example as a racemate, E/Z isomer mixture or cis/trans isomer mixture.

The aldehydes according to the invention are compounds which are generally stable for an extended period at room temperature and are in solid or liquid form.

The aldehydes according to the invention contain at least one difluorooxymethylene bridge and have a substituted phenyl radical at the molecule end opposite to the aldehyde function. This terminal radical A$^{14}$ is a substituted phenyl radical of the formula

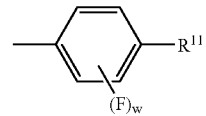

and preferably a substituted phenyl radical of the formula

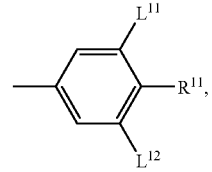

where w is 0, 1, 2, 3 or 4, L$^{11}$ and L$^{12}$, independently of one another, are H or F, and R$^{11}$ is H, F, Cl, Br, I, CN, —NCS, an O-aralkyl radical, or an alkyl radical having from 1 to 15 carbon atoms which is unsubstituted or mono- or polysubstituted by F, Cl, Br, I and/or —CN, where one or more CH$_2$ groups in this radical may each, independently of one another, be replaced by —C≡C—, —CH═CH—, —O—, —S—, —CO—, —CO—O— or —O—CO— in such a way that hetero atoms are not linked directly to one another. R$^{11}$ is preferably H or a polar radical, in particular F, Cl, OCF$_3$, OCHF$_2$ or CF$_3$. It is furthermore particularly preferred for either L$^{11}$ or L$^{12}$ or both substituents L$^{11}$ and L$^{12}$ to be F.

In certain preferred embodiments of the aldehydes according to the invention, Z$^{11}$, Z$^{12}$ and Z$^{13}$ in the above formula I are each, independently of one another, a single bond, —CH$_2$CH$_2$—, —CF$_2$CH$_2$—, —CH$_2$CF$_2$—, —CF$_2$CF$_2$— or —CF$_2$O—, where at least one of Z$^{11}$, Z$^{12}$ and Z$^{13}$ is —CF$_2$O—. If, for example, p and n in the above formula I are both zero, and the aldehyde of the formula I according to the invention thus contains neither an A$^{12}$-Z$^{12}$ group nor an A$^{13}$-Z$^{13}$ group, Z$^{11}$ is —CF$_2$O—. If, for example, n is 1 and p is 0, then either Z$^{11}$ or Z$^{12}$ is a difluorooxymethylene bridge, and the respective other bridge (Z$^{12}$ or Z$^{11}$) is then preferably a single bond, —CH$_2$CH$_2$—, —CF$_2$CH$_2$—, —CH$_2$CF$_2$— or —CF$_2$CF$_2$—, or both Z$^{11}$ and Z$^{12}$ are each a difluorooxymethylene bridge. Z$^{11}$, Z$^{12}$ and Z$^{13}$ are particularly preferably, independently of one another, a single bond or —CF$_2$O—, where at least one of the bridges Z$^{11}$, Z$^{12}$ and Z$^{13}$ is —CF$_2$O—.

In a further preferred embodiment of the present invention, Z$^{11}$ in the formula I is —CF$_2$O—. If m in the formula I is zero—which also applies to a further preferred embodiment of the invention—no ring $A^{11}$ is present in this embodiment between the functional CHO group and the bridge $Z^{11}$, and the —$CF_2O$— group is bonded directly to the carbonyl function of the aldehyde of the formula I according to the invention.

It is furthermore particularly preferred for n and p both to be 0, so that $Z^{11}$ is a difluorooxymethylene bridge.

Particularly preferred aldehydes of the present invention are the following aldehydes, which contain a ring $A^{14}$=

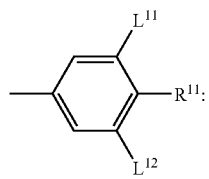

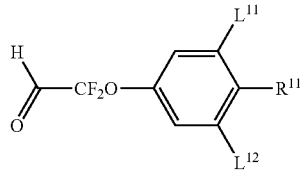
I-A

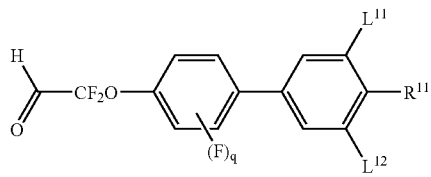
I-B

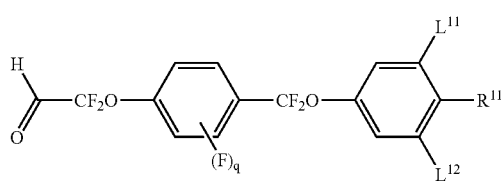
I-C

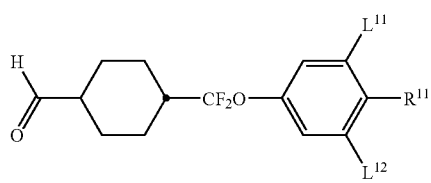
I-D

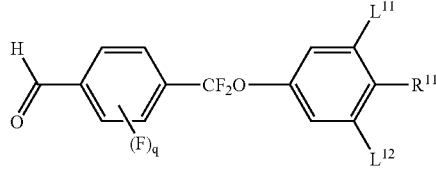
I-E

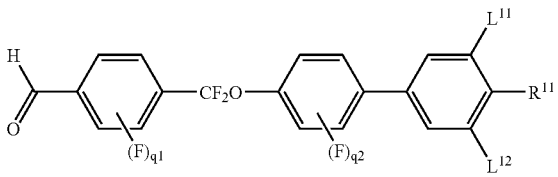
I-F

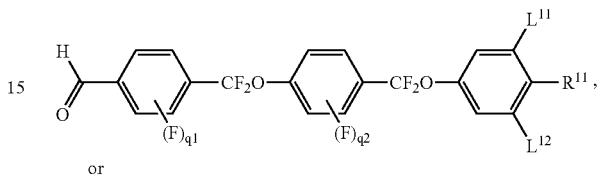
I-G or

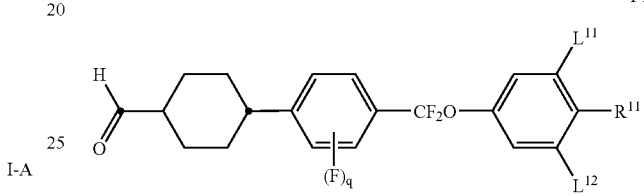
I-H

In the above-mentioned formulae I-A to I-H, the radical $R^{11}$ is as defined above for the formula I, while $L^{11}$ and $L^{12}$, independently of one another, are H or F. The q, q1 and q2 are, independently of one another, 0, 1, 2, 3 or 4, i.e. the corresponding 1,4-phenylene rings may each, independently of one another, contain no fluorine atoms or 1 fluorine atom in each of the free ring positions (2-, 3-, 5- and 6-positions) and contain in total up to 4 fluorine atoms; q, q1 and q2 are preferably, independently of one another, 0, 1 or 2, and the fluorine substituents—if present in the molecule—are preferably in the 3- or 5-position of the 1,4-phenylene ring (i.e. they have the same orientation as the substituents $L^{11}$ and $L^{12}$).

The aldehydes of the formulae I-A, I-B and I-C conform to the general formula I in that m is zero and $Z^{11}$ is —$CF_2O$—. In the formula I-A, n and p are also zero. In the formula I-B, p is zero, while n is 1, $A^{12}$ is an optionally fluorine-substituted 1,4-phenylene ring, and $Z^{12}$ is a single bond; formula I-C differs from formula I-B in that $Z^{12}$ is not a single bond, but instead a difluorooxymethylene bridge.

The aldehydes of the formulae I-D and I-E are derived from the general formula I in that m is 1, n and p are both 0, and $Z^{11}$ forms the difluorooxymethylene bridge; $A^{11}$ is either a (preferably trans-substituted) 1,4-cyclohexylene ring (I-D) or an optionally substituted 1,4-phenylene ring (I-E).

In the aldehydes of the formulae I-F and I-G, m and n are each 1, while p is zero; both $A^{11}$ and $A^{12}$ are each a 1,4-phenylene ring, while $Z^{12}$ is a single bond (I-F) or a $CF_2O$ bridge (I-G).

The aldehydes of the formula I-H conform to the general formula I in that m and n are 1, and p is 0, $Z^{11}$ is a single bond, and $Z^{12}$ is the $CF_2O$ bridge, $A^{11}$ is a (preferably trans-substituted) 1,4-cyclohexylene ring, and $A^{12}$ is an optionally fluorinated 1,4-phenylene ring.

In the aldehydes of the formulae I-A to I-H, $R^{11}$ is preferably a polar radical, particularly preferably F, Cl, $OCF_3$, $OCHF_2$ or $CF_3$, in particular F. $L^{11}$ and $L^{12}$ are, independently of one another, H or F; preferably, at least one of $L^{11}$ and $L^{12}$ is F, and particularly preferably both substituents $L^{11}$ and $L^{12}$ are F. The q, q1 and q2 are preferably each 2.

Of the preferred aldehydes of the formulae I-A to I-H, particular preference is given to aldehydes of the formulae I-A, I-D, I-E and I-H, in particular aldehydes of the formula I-D.

Examples of particularly preferred aldehydes of the formula I-A are:

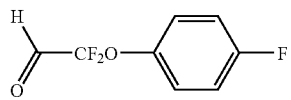
I-A1

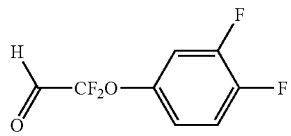
I-A2

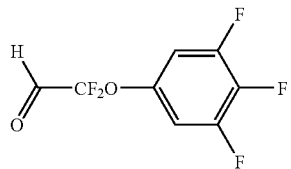
I-A3

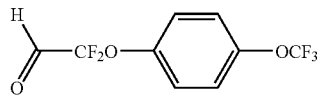
I-A4

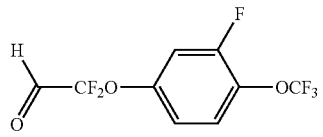
I-A5

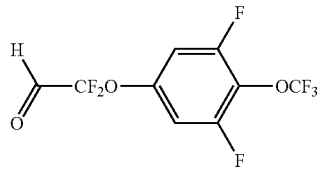
I-A6

Examples of particularly preferred aldehydes of the formula I-D are:

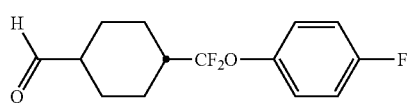
I-D1

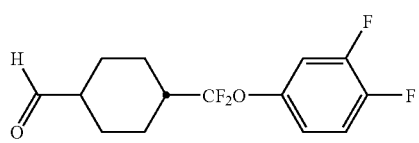
I-D2

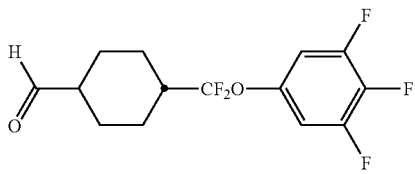
I-D3

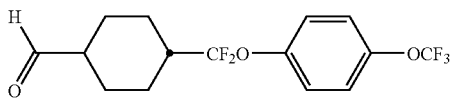
I-D4

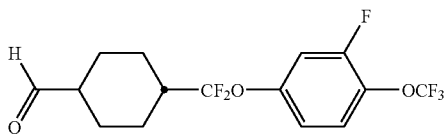
I-D5

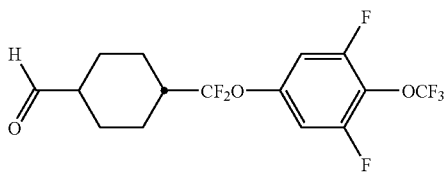
I-D6

Examples of particularly preferred aldehydes of the formula I-E are:

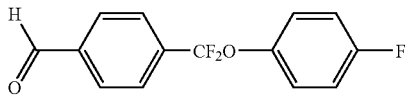
I-E1

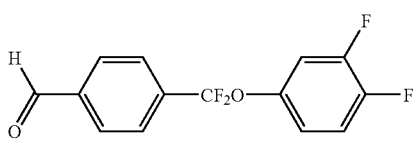
I-E2

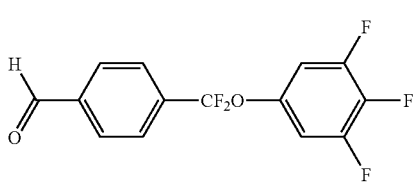
I-E3

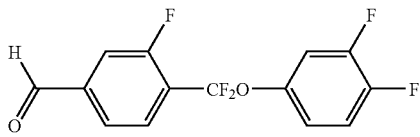
I-E4

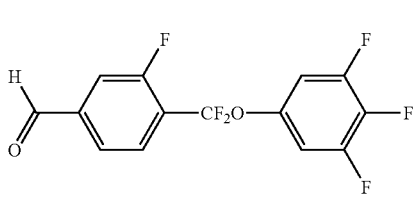
I-E5

-continued

I-E6
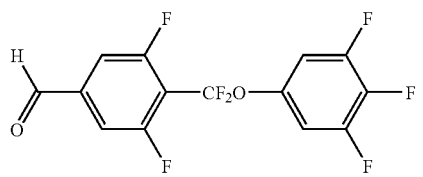

I-E7
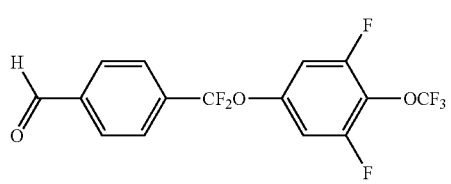

I-E8
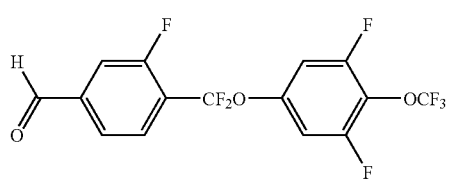

I-E9
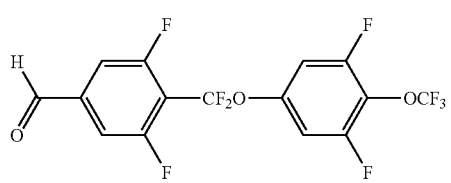

Examples of particularly preferred aldehydes of the formula I-H are:

I-H1
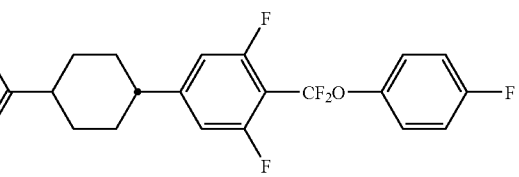

I-H2
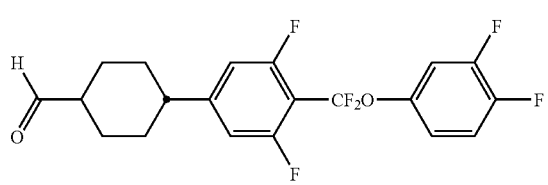

I-H3
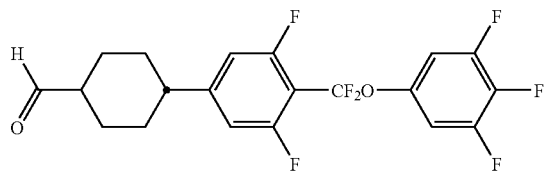

-continued

I-H4
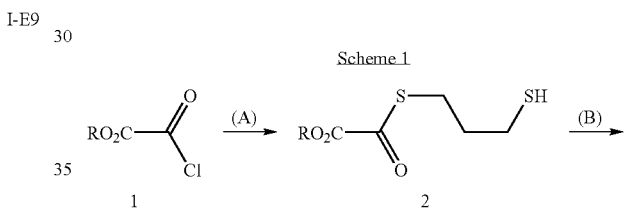

The aldehydes according to the invention are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

Thus, aldehydes of the formula I-A are preparable in a simple manner and in good yields from commercially available or literature-known starting compounds, for example, in accordance with scheme 1 below:

Scheme 1

The conversion of 1 (R is an alkyl or benzyl radical) into 2 in step (A) is carried out using $NaS-(CH_2)_3-SH$. 2 is converted into 3 using trifluoromethanesulfonic acid (analogously to the processes of P. Kirsch et al., Angew. Chem. 2001, 113,1528; see also WO 01/64667) in step (B). In step (C), the oxidative fluorodesulfuration (as described by P. Kirsch et al., Angew. Chem. 2001, 113, 1528, and WO 01/64667) is then carried out by converting 3 into 4, initially at low temperatures, using $NEt_3 \cdot 3$ HF (Et=ethyl) and a phenol of the formula

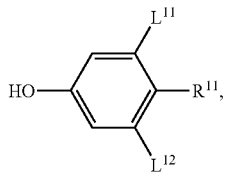

then using 1,3-dibromo-5,5-dimethylhydantoin (DBH) or N-bromosuccinimide (NBS) or bromine, and finally using aqueous lye. In step (D), the aldehyde function is introduced, giving compound I-A according to the invention, either by direct reduction of the ester using a suitable reducing agent, such as DIBAL-H (diisobutylaluminium hydride), in an inert solvent, for example n-heptane, or by reduction of the ester to the corresponding alcohol and subsequent oxidation to the aldehyde using a suitable oxidising agent, for example using Dess-Martin reagent.

An alternative synthesis is shown in scheme 2:

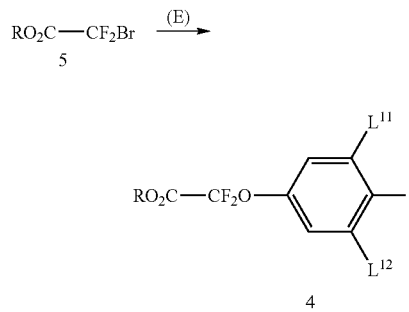

Compound 5 (where R=unsubstituted alkanyl or benzyl) is converted into compound 4, which is known from scheme 1, using a phenoxide of the formula

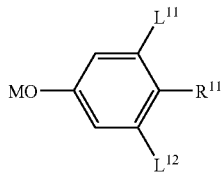

(where M=Na, K or Cs), and this is then converted into the aldehyde of the formula I-A according to the invention as shown in scheme 1. Process step (E) can be carried out in various ways.

One variant includes reacting the phenoxide with 4 in an ethereal solvent, for example tetrahydrofuran (THF), in the presence of hexamethylphosphoric triamide (HMPT). In another variant, the reaction of the phenoxide with 4 is carried out with catalysis by a Pd⁰ catalyst, which can be formed, for example, in situ from bis(tricyclohexylphosphine)palladium dichloride.

The aldehydes of the formula I-B according to the invention are also preparable analogously to schemes 1 and 2 by reacting the biphenyl of the formula

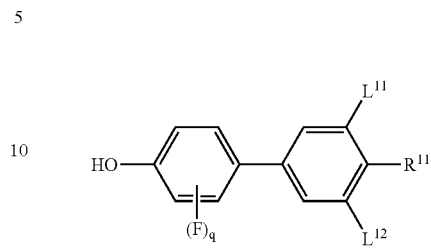

(in which $R^{11}$, $L^{11}$, $L^{12}$ and q are as defined for the formula I) with compound 3 in process step (C) in scheme 1 or reacting the corresponding alkoxide with compound 5 in process step (E) in scheme 2.

Aldehydes of the formula I-C according to the invention are preparable, for example, as shown in scheme 3:

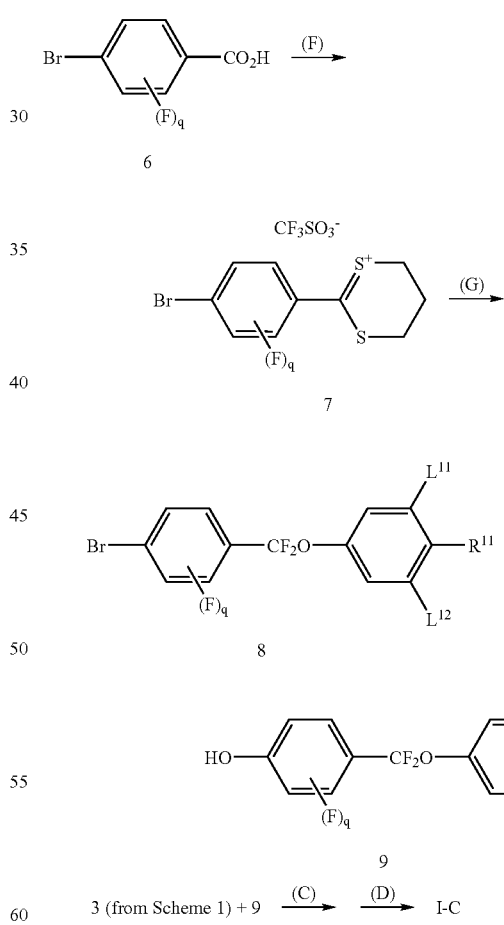

The optionally fluorinated 4-bromobenzoic acid (6) is converted into compound 7 under conditions which have been described, for example, by P. Kirsch et al., Angew. Chem. 2001, 113, 1528, (see also explanations for scheme 1 above), and this is itself subjected to oxidative fluorodesulfuration (as described by P. Kirsch et al., Angew. Chem. 2001, 113, 1528, and WO 01/64667) ((G)) using the phenol

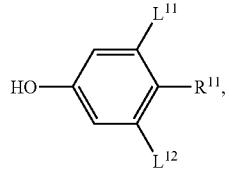

with formation of compound 8 containing a difluorooxymethylene bridge. Conversion into the phenol 9 is then carried out, for example, by lithiation using n-butyllithium, subsequent formation of the corresponding boronic acid using trimethyl borate (or another boronic acid derivative), and final reaction with hydrogen peroxide with conversion of the —B(OH)$_2$ group into the —OH group of the phenol 9 (step (H)). This phenol is then converted into the aldehyde I-C according to the invention in a second fluorodesulfuration reaction under comparable conditions using the synthone 3 prepared as shown in scheme 1.

Alternatively, the phenoxide of compound 9 can be converted into the aldehyde I-C analogously to the process as shown in Scheme 2 in reaction steps (E) and (D) using compound 5.

Aldehydes of the formula I-D according to the invention are preparable, for example, as shown in scheme 4:

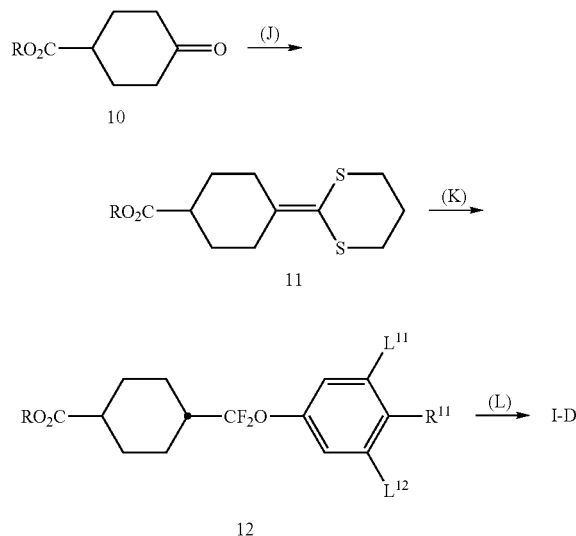

The conversion of the 4-cyclohexanonecarboxylic acid ester 10 (R is an unsubstituted alkanyl or benzyl radical) into 11 ((J)) is carried out by the above-mentioned process of P. Kirsch et al., Angew. Chem. 2001, 113, 1528, or in accordance with the process of J. Mlynarski and A. Banaszek, Tetrahedron 55 (1999) 2785, by reaction with trimethylsilyl-1,3-dithiane in THF in the presence of n-butyllithium in hexane at low temperatures. The subsequent oxidative fluorodesulfuration of 11 to 12 (cf. also P. Kirsch et al., Angew. Chem. 2001, 113, 1528) ((K)) and the final reduction ((L)) to give the aldehyde I-D according to the invention are carried out analogously to the synthetic processes described above. If the cis isomer is obtained in addition to the preferred trans-cyclohexane derivative 12 in individual cases in reaction step (K), conversion of the cis isomer into the trans isomer or removal thereof from the product mixture is carried out by means of known methods, for example by recrystallisation or in the case of liquid compounds by fractional distillation.

The isomerisation can also be carried out by treatment of the cis/trans isomer mixture with a base, for example sodium hydroxide, in a suitable solvent, for example an alcohol, such as methanol, or in mixtures of methanol, tetrahydrofuran and water.

Aldehydes of the formula I-E according to the invention are preparable, for example, as shown in scheme 5:

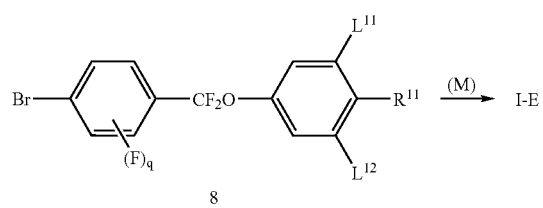

The bromide 8, which is preparable as shown in scheme 3, is converted into the aldehyde I-E according to the invention, for example, by halogen-metal exchange using an organometallic base, for example n-butyllithium, and reaction with a formylating reagent, such as N,N-dimethylformamide or N-formylpiperidine. A preferred variant of reaction step (M) includes exchange of the bromine in compound 8 by halogen-magnesium exchange using isopropylmagnesium chloride or bromide against MgCl or MgBr and scavenging of the arylmagnesium halide formed in this way with the formylating reagent. Alternatively, the bromide 8 can first be converted into the corresponding nitrile using CuCN/N-methylpyrrolidone, and this nitrile is subsequently subjected to reduction using a suitable reducing agent, such as DIBAL-H or bis(cyclopentadienyl)zirconium chloride hydride, to give the aldehyde I-E.

Aldehydes of the formula I-F according to the invention are preparable, for example, as shown in scheme 6:

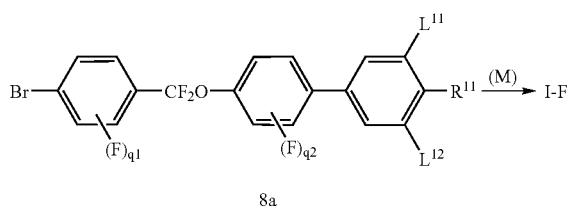

The conversion of the bromide 8a here into I-F corresponds to that of the bromide 8 into I-E from scheme 5; the bromide 8a is preparable like the bromide 8 as shown in scheme 3, step (G), but with compound 7 being reacted with the biphenyl compound

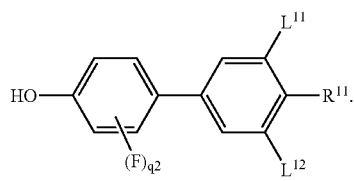

Aldehydes of the formula I-G according to the invention are preparable, for example, analogously to the preparation of the aldehydes I-C by corresponding reaction of a bromide of the formula 7 with a phenol of the formula 9 and subsequent formylation of the bromide via bromine-metal exchange and scavenging reaction with a formylating reagent.

Aldehydes of the formula I-H according to the invention are obtainable, for example, as shown in scheme 7:

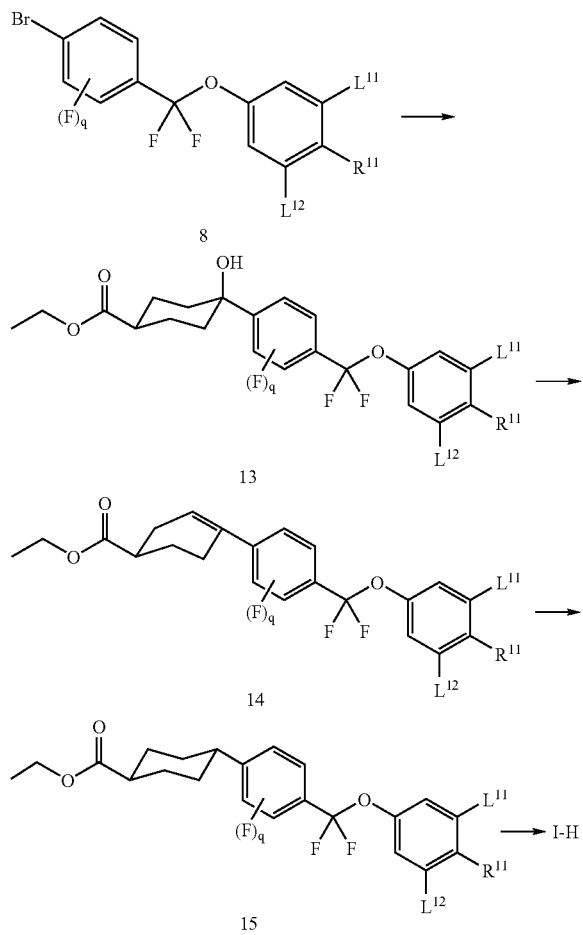

The bromide 8 is metallated using an organometallic base, for example isopropylmagnesium chloride, and converted into the ester 13 using ethyl cyclohexan-4-onecarboxylate. A suitable water-eliminating reagent, for example catalytic amounts of a strong acid, such as sulfuric acid, is used to carry out the elimination to give 14, which is hydrogenated to the ester 15 with transition-metal catalysis, for example using platinum metal. If necessary, the isomerisation of any cis-15 formed to trans-IS can be carried out by conventional methods (for example treatment with base, for example NaOH, in a suitable solvent) at this stage. Finally, the reduction to I-H is carried out using, for example, diisobutylaluminium hydride. Any requisite isomerisation of product having the cis-configuration on the cyclohexane ring to trans-I-H can likewise be carried out by known methods (for example treatment with methanolic sodium hydroxide solution) at the end stage. Further aldehydes of the formula I according to the invention are—as the person skilled in the art can readily recognise—preparable by adaptation of the processes described above and using further processes known from the prior art. Possible or requisite modifications may relate, for example, to aldehydes of the formula I in which, for example, $Z^{13}$ is a —CO—O— group. For example, an aldehyde $$OHC-A^{11}-CF_2O-A^{13}-Br$$

can firstly be built up from the ester $$ethyl-O_2C-A^{11}-CF_2O-A^{13}-Br$$

in accordance with a process described in greater detail above, where the bromide on the "right-hand" side of the molecule is inert under the reaction conditions under which the ethyl ester on the "left-hand" side of the molecule is converted into the aldehyde function. After introduction of the aldehyde function and, if desired, protection of the carbonyl function, for example as the acetal, halogen-metal exchange, for example, subsequent reaction with $CO_2$ and finally esterification using an alcohol of the formula HO-$A^{14}$ after removal of any protecting group present can be carried out to give the aldehyde according to the invention $$OHC-A^{11}-CF_2O-A^{13}-CO_2-A^{14}$$

The aldehydes according to the invention can be used as synthones for the synthesis of more complex compounds containing a difluorooxymethylene bridge, in particular mesogenic compounds. The present invention therefore furthermore relates to a process for the preparation of 1,3-dioxane compounds using the aldehydes of the general formula I according to the invention, which are reacted with suitable 1,3-diols or 1,3-bissilylated derivatives of these diols.

These diols or their bissilylated derivatives are preferably those of the general formula II

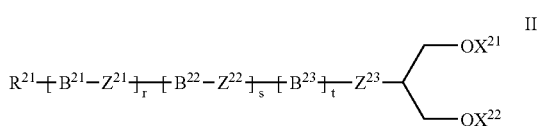

where r, s and t, independently of one another, are 0 or 1;

$R^{21}$ is an alkyl radical having from 1 to 15 carbon atoms which is unsubstituted or mono- or polysubstituted by F, Cl, Br, I and/or —CN, where one or more $CH_2$ groups in this radical may each, independently of one another, be replaced by —C≡C—, —CH=CH—, —O—, —S—, —CO—, —CO—O— or —O—CO— in such a way that hetero atoms are not linked directly to one another;

$B^{21}$, $B^{22}$ and $B^{23}$, independently of one another, are

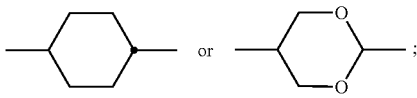

$Z^{21}$, $Z^{22}$ and $Z^{23}$, independently of one another, are a single bond, —$CH_2CH_2$—, —$CF_2CH_2$—, —$CH_2CF_2$—, —$CF_2CF_2$—, —CH=CH— or —C≡C—;

$X^{21}$ and $X^{22}$ are H or $SiR^{22}R^{23}R^{24}$, where $R^{22}$, $R^{23}$ and $R^{24}$ are each, independently of one another, an alkanyl radical having from 1 to 6 carbon atoms, and one or two of the radicals $R^{22}$, $R^{23}$ and $R^{24}$ may also be phenyl;

so that the reaction with the aldehydes of the formula I gives dioxane compounds of the general formula III:

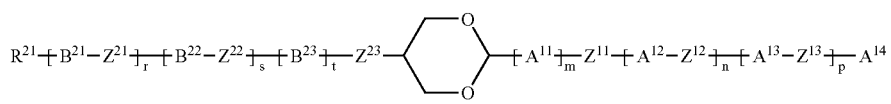

III in which $R^{21}$, $A^{11}$, $A^{12}$, $A^{13}$, $A^{14}$, $B^{21}$, $B^{22}$, $B^{23}$, $Z^{11}$, $Z^{12}$, $Z^{13}$, $Z^{21}$, $Z^{22}$, $Z^{23}$, m, n, p, r, s and t are as defined for the formulae I and II.

In a preferred embodiment of the process according to the invention, the aldehyde employed has the structure of the formula Ia:

OHC-$(A^{11})_m$-$CF_2O$-$(A^{12}$-$Z^{12})_n$-$(A^{13}$-$Z^{13})_p$-$A^{14}$     Ia where m is either zero or 1, and $A^{11}$ is at the same time a 1,4-cyclohexylene ring; $A^{12}$, $A^{13}$, $A^{14}$, $Z^{12}$, $Z^{13}$, n and p are as defined in one of Claims 1 to 7.

The 1,3-diols and their bissilylated derivatives are likewise prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The preparation of numerous 1,3-diols and their bissilylated derivatives is also described, inter alia, in P. Kirsch and E. Poetsch, Adv. Mater. 1998, 10, 602, and references cited therein. Preferred dioxanes of the formula III are those having a trans-configuration of the central dioxane ring

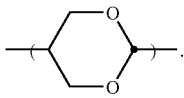

They are obtained either directly in isomerically pure form on reaction of aldehydes of the formula I with compounds of the formula II or after separation of the cis/trans isomers, for example by recrystallisation. If the diols or diol derivatives employed are compounds which already contain a trans-linked cyclohexane or 1,3-dioxane ring, the desired central trans-1,3-dioxane ring frequently forms in a large isomeric excess or exclusively.

The reaction according to the invention of the aldehydes of the formula I according to the invention with diols or diol derivatives, preferably of the formula II, is carried out under conventional conditions for acetal formation. If a diol of the formula II where $X^{21}$=$X^{22}$=H is employed, the reaction with the aldehyde of the formula I can be carried out in an inert solvent, usually at the boiling point, with acid catalysis and removal of the resultant water by distillation. Suitable solvents are aromatic solvents, in particular toluene and xylenes. The acid catalyst used is usually a Lewis acid or an inorganic or organic protonic acid, with p-toluenesulfonic acid being particularly preferred. The reaction time is not crucial per se; it is usually between 30 minutes and 18 hours, depending on the rate of the condensation reaction.

Bissilylated diol derivatives, preferably of the formula II where $X^{21}$=$X^{22}$=$SiR^{22}R^{23}R^{24}$, are preferably employed for the reaction with aldehydes of the formula I if the compound of the formula I or the compound of the formula II or both contain acid-sensitive groups, for example a 1,3-dioxane ring. The reaction is then preferably carried out under aprotic conditions in the presence of a catalytic amount of a water- and proton-free acid, for example trimethylsilyl triflate (($methyl)_3SiOSO_2CF_3$), in an inert solvent, for example dichloromethane, preferably at temperatures below room temperature, for example at −78° C. Here too, the reaction time is not crucial per se; it is usually between 15 or 30 minutes and 18 hours, depending on the rate of the reaction, which is usually significantly faster than in the case of the diols.

Bissilylated compounds of the formula II are preparable from the corresponding 1,3-diols by conventional processes (see, for example, P. Kirsch and E. Poetsch, Adv. Mater. 1998, 10, 602, and references cited therein). Particular preference is given to the diol derivatives of the formula II which contain trimethylsilyl protecting groups ($X^{21}$=$X^{22}$=trimethylsilyl, $SiMe_3$). They are introduced, for example, by reaction of the corresponding diol with excess trimethylsilyl chloride in the presence of triethylamine in N,N-dimethylformamide at temperatures between OOC and room temperature for, for example, 18 hours.

The 1,3-dioxanes which are preparable by the process according to the invention have advantageous properties—for example a large dielectric anisotropy $\Delta \in$ at the same time as comparatively low rotational viscosity $\gamma_1$—and are therefore widely used in liquid-crystalline media, in particular for electro-optical applications.

The examples below further illustrate the present invention without restricting it in its scope.

Above and below, percentage data are per cent by weight. All temperatures are given in degrees Celsius. m.p. denotes melting point, cl.p. clearing point. Furthermore, C=crystalline state, N=nematic phase, S=smectic phase and I=isotropic phase. $S_c$ denotes a smectic C phase. $\Delta n$ denotes the optical anisotropy ($\Delta n = n_e - n_o$, where $n_e$ is the refractive index of the extraordinary ray and $n_o$ is the refractive index of the ordinary ray) (589 nm, 20° C.). $\Delta \in$ denotes the dielectric anisotropy ($\Delta \in = \in_\| - \in_\perp$, where $\in_\|$ denotes the dielectric constant parallel to the longitudinal molecular axes and ∈⊥ denotes the dielectric constant perpendicular thereto) (1 kHz, 20° C.). The optical data were measured at 20° C., unless expressly stated otherwise. The rotational viscosity γ₁ [mPa·s] was likewise determined at 20° C. SR denotes the specific resistance [Ω·cm], VHR the voltage holding ratio. The physical parameters were determined experimentally as described in "Licristal, Physical Properties Of Liquid Crystals, Description of the measurement methods", ed. W. Becker, Merck KGaA, Darmstadt, revised edition, 1998, with the properties of individual compounds in some cases being determined after measurement of a defined amount of compound (usually 10% by weight) in a defined host mixture having known properties, followed by extrapolation.

EXAMPLES

Example 1

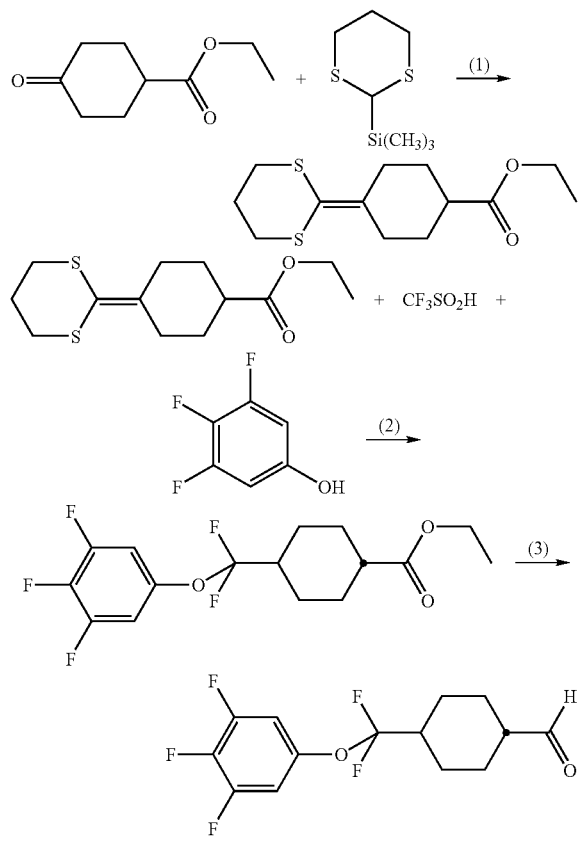

Step (1): 230.90 g of 2-trimethylsilyl-1,3-dithiane (1.20 mol) are dissolved in THF and cooled to −70° C., and 769.33 ml (1.26 mol) of n-butyllithium (15% solution in n-hexane) are added dropwise. The mixture is allowed to warm to 0° C. over the course of 3 hours, re-cooled to −70° C. and carefully added dropwise to a solution, cooled to −70° C., of 204.25 g (1.20 mol) of ethyl 4-cyclohexanonecarboxylate in 900 ml of THF. When the addition is complete, the cooling is removed, and the mixture is allowed to warm to room temperature. The reaction mixture is poured into ice-water and extracted with heptane. The combined organic phases are washed with sat. NaCl solution and concentrated, and the yellow oil obtained in this way is recrystallised from pen-tane. Pale-yellow crystals of the ketene dithioketal (78% yield), which are employed in step (2) without further purification.

Step (2): The ketene dithioketal from step (1) (128.10 g, 0.47 mol) is dissolved in dichloromethane, and 41.30 ml (0.47 mol) of trifluoromethanesulfonic acid are added dropwise with ice cooling. After 15 minutes, the cooling is removed, and the mixture is stirred at room temperature for 1 hour. The mixture is subsequently cooled to −70° C., a mixture of triethylamine (117.03 ml, 0.84 mol) and 3,4,5-trifluorophenol (104.53 g, 0.71 mol) in dichloromethane is added, and the mixture is stirred at −70° C. for 1 hour. 379.22 ml (2.35 mol) of triethylamine hydrofluoride are then added, and, after 5 minutes, bromine (120.48 ml, 2.35 mol) in dichloromethane is added over the course of 20 minutes. The mixture is allowed to stir for a further 1 hour, and the batch is allowed to warm to −10° C. The solution is then added with stirring to a mixture of 400 ml of sat. sodium hydrogensulfite solution, 5 l of machine ice and 800 ml of 32% sodium hydroxide solution. The organic phase is separated off, and the aqueous phase is post-extracted once with dichloromethane. The combined organic extract is washed with saline solution and evaporated to give a residue, which is extracted with heptane and evaporated in a rotary evaporator.

The residue obtained in this way is taken up in toluene/heptane=1:1 and filtered through silica gel. The eluate is evaporated in a rotary evaporator, and the residue is subjected to fractional distillation under reduced pressure. The fraction of the desired product (cis/trans mixture) is recrystallised from cold pentane, giving 41.6 g (24.5%) of the trans product in a purity which is sufficient for the further reaction.

For analytical purposes, 5 g of the crude product are again taken up in toluene/heptane=1:1 and filtered through basic aluminium oxide. The purity of the solid obtained after evaporation in a rotary evaporator and recrystallisation is 99.3% of trans product (m.p.: 39° C.) according to GC.

Step (3): The ester obtained in step (1) (77.50 g, 0.220 mol) is dissolved in toluene and cooled to −70° C. At this temperature, 261.00 ml (0.261 mol) of diisobutylaluminium hydride (DIBAH, 1M solution in toluene, 0.261 mol) are added dropwise. The reaction solution is stirred for a further 1 hour and then poured cold into saturated ammonium chloride solution. The organic phase is separated off and washed again with dilute hydrochloric acid, dried, filtered and evaporated. Quantitative yield.

Example 2

Example 2a

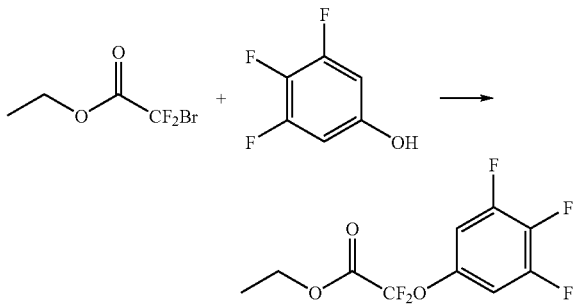

Sodium hydride (60% suspension in mineral oil, 100.00 g, 2.50 mol) is initially introduced in tetrahydrofuran (THF) under a nitrogen atmosphere. A solution of 3,4,5-trifluorophenol (386.00 g, 2.50 mol) in THF is added dropwise thereto over the course of 2 hours with gentle ice-water cooling. The resultant suspension is stirred for a further 1 hour. Hexamethylphosphoric triamide (22.50 ml, 0.13 mol) is subsequently added dropwise. The mixture is stirred at room temperature for a further 10 minutes, giving solution 1.

Ethyl bromodifluoroacetate (366.00 ml, 2.50 mol) is dissolved in THF and added dropwise to solution 1. The reaction mixture is warmed to 60° C. and stirred at this temperature for 16 hours. The mixture is evaporated, and the residue is taken up in toluene/pentane=1:1 and filtered through silica gel. After vacuum distillation and recrystallisation, the desired ester is obtained in a yield of 50% and employed without further purification.

Example 2b

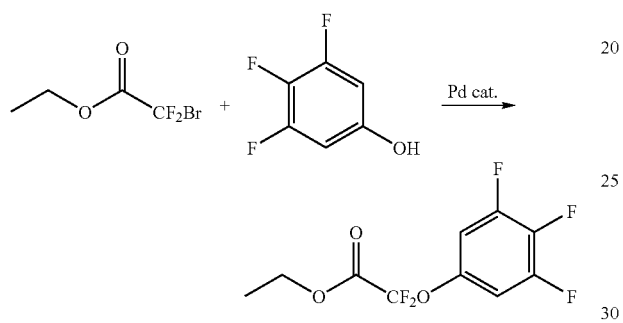

Sodium hydride (60% suspension in mineral oil, 10.00 g, 0.25 mol) is initially introduced in diethylene glycol dimethyl ether. 3,4,5-Trifluorophenol (38.60 g, 0.25 mol), dissolved in diethylene glycol dimethyl ether, is added dropwise to the sodium hydride suspension. The mixture is subsequently stirred at room temperature for a further 1 hour (solution 1). During this time, the catalyst (bis(tricyclohexylphosphine)palladium dichloride (3.70 g, 0.005 mol) is initially introduced in diethylene glycol dimethyl ether and pre-reduced under a nitrogen atmosphere using 10 ml of DIBAH (1M in dichloromethane). The catalyst solution is added to solution 1, and ethyl bromodifluoroacetate (36.60 ml, 0.25 mol) is added dropwise over the course of 10 minutes. The reaction solution is warmed to 80° C. and held at this temperature for two hours, then cooled to room temperature and poured into ice-water. The mixture is extracted three times with methyl t-butyl ether (MTBE). The combined organic extracts are washed with water, dried and filtered. The residue is evaporated and then subjected to fractional distillation under reduced pressure. Yield of the desired product: 48%. The product obtained is employed without further purification.

Example 3

Example 3a

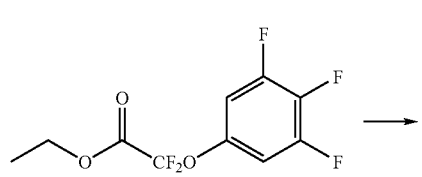

-continued

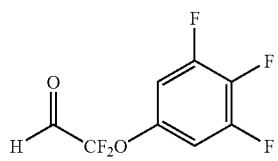

The ester prepared in Example 2a or Example 2b (0.10 mol) is dissolved in n-hexane and cooled to −70° C. DIBAH in hexane (0.10 mol) is added dropwise at this temperature, and the mixture is stirred for a further 4 hours. The mixture is allowed to warm to room temperature and is stirred for a further 96 hours. The cold reaction solution is poured into cold 18% hydrochloric acid. The organic phase is separated off and again washed with water, dried, filtered and subjected to fractional distillation. The aldehyde according to the invention boils below the boiling point of the starting ester and is obtained in adequate purity for the further reactions.

Example 3b

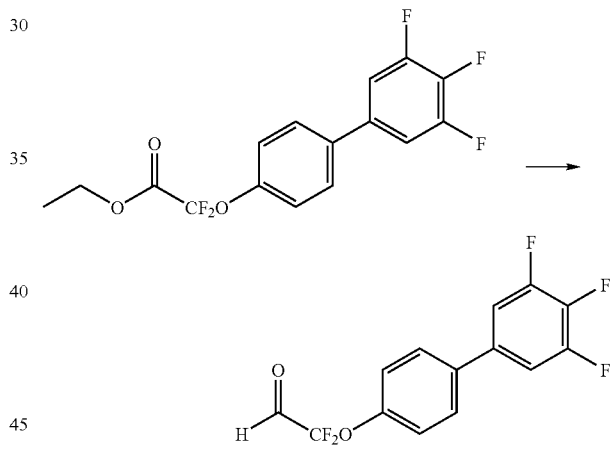

The aldehyde is prepared analogously to Example 3a. The aldehyde is obtained in adequate purity for the further reactions.

Example 4

Example 4a

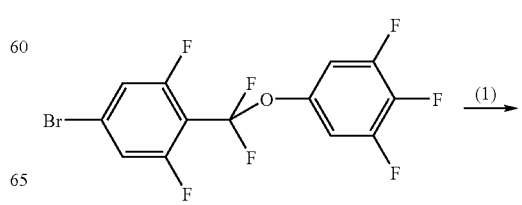

-continued

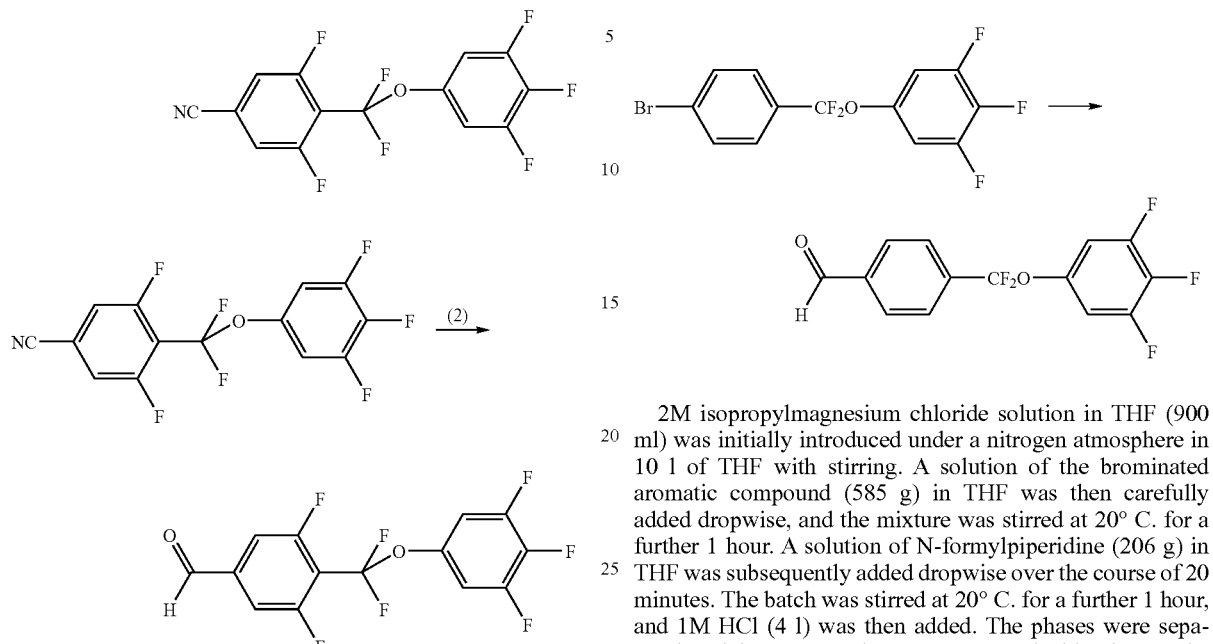

Step (1): 1-Methyl-2-pyrrolidone (2.4 kg) is initially introduced. For drying, about 500 ml are distilled off under reduced pressure. The bromide (0.512 mol) and copper(I) cyanide (0.666 mol) are then added. The mixture is warmed at 150° C. until the reaction is complete. After the 1-methyl-2-pyrrolidone has been distilled off, methyl tert-butyl ether is added, and the mixture is extracted with water. The organic phase is evaporated, and the residue is taken up in toluene/heptane and filtered through silica gel. The crude product obtained is recrystallised from heptane.

Step (2):

Variant A: The product from step (1) (0.015 mol) is initially introduced in toluene and cooled to −70° C. A solution of diisobutylaluminium hydride in toluene (0.015 mol) is slowly added dropwise at such a rate that the temperature does not rise above −70° C. When the reaction is complete, the mixture is poured into cold hydrochloric acid (18%), a little methyl tert-butyl ether is added, and the organic phase is separated off, dried over sodium sulfate, filtered and evaporated. The aldehyde obtained in this way is employed without further purification.

Variant B: The product from step (1) (0.015 mol) is initially introduced in tetrahydrofuran and cooled to 0° C. A solution of bis(cyclopentadienyl)zirconium chloride hydride in tetrahydrofuran (0.015 mol) is slowly added dropwise at such a rate that the temperature does not rise above 0° C. The mixture is stirred at 0° C. for 1 hour and then at room temperature until the reaction is complete and is poured into cold hydrochloric acid, a little methyl tert-butyl ether is added, and the organic phase is separated off, dried, filtered and evaporated. The aldehyde obtained in this way is employed without further purification.

Example 4b 2M isopropylmagnesium chloride solution in THF (900 ml) was initially introduced under a nitrogen atmosphere in 10 l of THF with stirring. A solution of the brominated aromatic compound (585 g) in THF was then carefully added dropwise, and the mixture was stirred at 20° C. for a further 1 hour. A solution of N-formylpiperidine (206 g) in THF was subsequently added dropwise over the course of 20 minutes. The batch was stirred at 20° C. for a further 1 hour, and 1M HCl (4 l) was then added. The phases were separated, and the aqueous phase was extracted with toluene. The combined organic phases were washed with water, dried, filtered and evaporated under reduced pressure.

The oily residue was stirred with petroleum ether, during which pale-yellow crystals precipitated, which were filtered off with suction, washed and dried. Further product crystallised from the mother liquor and was likewise filtered off with suction, washed and dried. Pale-yellow crystals, m.p. 47–50° C.

Yield (not optimised): 337 g (77%).

Example 5

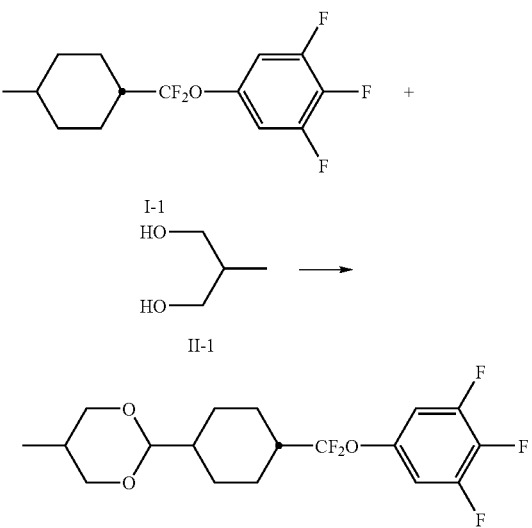

2.80 g (31.10 mmol) of 2-methyl-1,3-propanediol (II-1), 9.60 g (31.14 mmol) of the aldehyde I-1 from Example 1 and 0.63 g (3.30 mmol) of p-toluenesulfonic acid are dissolved in toluene and refluxed on a water separator for 30 minutes. After cooling to room temperature, the mixture is washed with water and then with sat. NaHCO$_3$ solution. The organic phase is evaporated. The residue which remains is taken up in toluene/heptane=1:1 and filtered through silica gel, and the eluate is re-evaporated under reduced pressure. After recrystallisation from heptane, the solid is dissolved in toluene/heptane and filtered through silica gel and basic aluminium oxide. Evaporation under reduced pressure and recrystallisation from heptane again gives trans-III-1 (3.3 g), which is pure according to HPLC analysis.

Examples 6–10

The dioxanes III-2 to III-6 are prepared analogously to Example 5:

Physical properties of the dioxanes III-1 to III-4 are shown in the following table.

TABLE

| Dioxane | Δn | Δε | Cl.p. [° C.] | γ$_1$ [mPa · s] |
|---|---|---|---|---|
| III-1 | 0.0689 | 22.7 | 7.9 | not determined |
| III-2 | 0.0618 | 21.3 | 27.9 | not determined |
| III-3 | 0.0688 | 20.6 | 45.3 | 207 |
| III-4 | 0.0642 | 20.1 | 54.8 | 229 |

Example 11

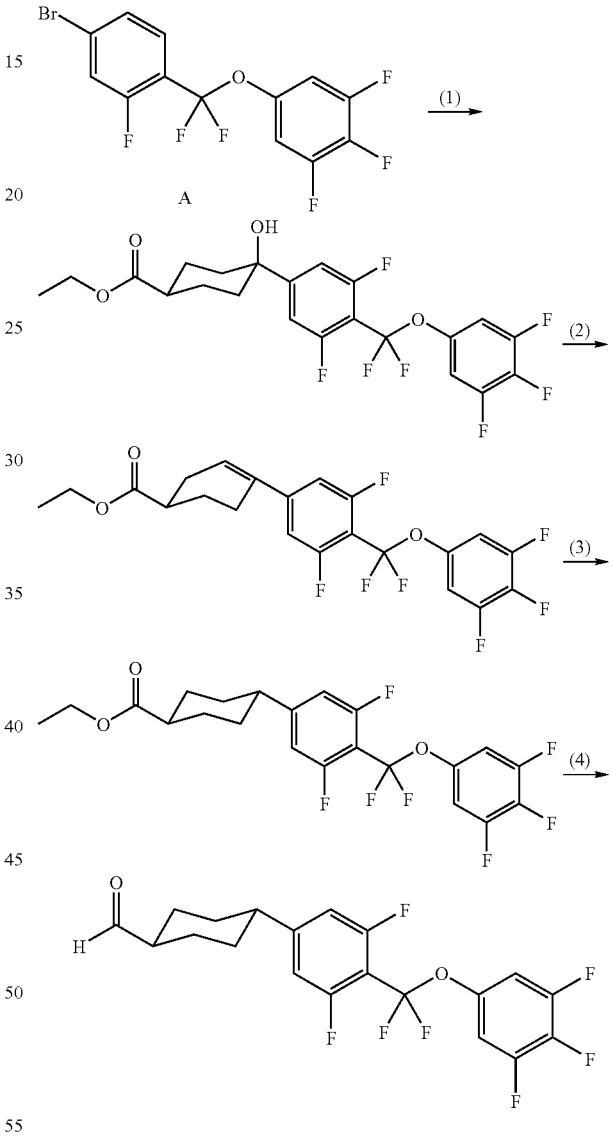

Step 1:

A solution of 58 g of the brominated aromatic compound A in THF is added dropwise to a solution of 1.2 equivalents of isopropylmagnesium chloride in THF at ~20° C. The reaction solution is stirred at room temperature for about a further 40 minutes. The mixture is then added dropwise to a solution of 1 equivalent of ethyl cyclohexan-4-onecarboxylate in THF at room temperature with water cooling. Stirring of the reaction is continued. The mixture is subsequently decomposed using dilute HCl solution, the phases are separated, and the organic phase is washed with water and evaporated to dryness under reduced pressure. The crude product (76 g) can be employed in the next step without further purification.

Step 2:

A solution of 26 g of the product from step 1 in toluene is warmed to ~70° C., and 1 g of 95%–98% sulfuric acid is added. The reaction solution is stirred at ~80° C. for about 3 hours. The solution is cooled, and water is added at ~45° C. The aqueous phase is separated off, and the organic phase is washed with water and evaporated to dryness under reduced pressure. For purification, the crude product is chromatographed over silica gel using toluene. The product-containing fractions are evaporated to dryness in a rotary evaporator. The product (14 g) can be employed in the next step without further purification.

Step 3:

A solution of 10 g of the product from step 2 in THF is hydrogenated for about 17 hours without pressure using 5% Pt/C. The hydrogenation solution is evaporated to dryness under reduced pressure, and the crude product is filtered through silica gel with toluene. The product-containing fractions are again evaporated to dryness under reduced pressure in a rotary evaporator. The product (9.8 g) can be employed in the next step without further purification.

Step 4:

A solution of 6.5 g of the product from step 3 in toluene/THF 4:1 (w/w) is cooled to about −76° C., and 1.2 equivalents of a 20% solution of diisobutylaluminium hydride in n-hexane are slowly added dropwise at this temperature. After about 4.5 hours, the reaction solution is introduced dropwise into a cold aqueous ammonium chloride solution, and the mixture is stirred for about 5 minutes. The phases are then separated, the aqueous phase is post-extracted with toluene, and the combined organic phases are washed firstly with 1N HCl solution and then with water. The organic phase is evaporated to dryness under reduced pressure. The crude product is purified by chromatography on silica gel using toluene/EtOAc 9:1. The product-containing fractions are evaporated to dryness under reduced pressure in a rotary evaporator. The cis/trans isomer mixture is isomerised in methanol using 0.1 equivalent of NaOH as base. Toluene and water are added to the mixture, the phases are separated, and the organic phase is washed with water and evaporated to dryness under reduced pressure. Crystallisation from isopropanol, chromatographic purification of the mother-liquor residues and crystallisation from isopropanol again gives the pure trans compound. Yield: 3.8 g.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10324313.5, filed May 27, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An aldehyde of formula I $$\text{OHC-}(A^{11})_m\text{-}Z^{11}\text{-}(A^{11}\text{-}Z^{12})_n\text{-}(A^{13}\text{-}Z^{13})_p\text{-}A^{14} \qquad \text{I}$$

wherein $A^{11}$ is

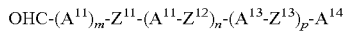

$A^{12}$ and $A^{13}$ are, independently of one another,

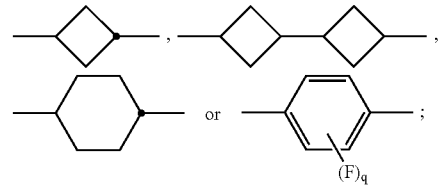

$A^{14}$ is

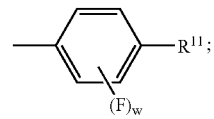

$Z^{11}$ is —CF$_2$O—;
$Z^{12}$ and $Z^{13}$ are, independently of one another, a single bond, —CH$_2$CH$_2$—, —CF$_2$CH$_2$—, —CH$_2$CF$_2$—, —CF$_2$CF$_2$—, —CH=CH—, —C≡C—, —CO—O—, —O—CO—, —CH$_2$O—, —OCH$_2$— or —CF$_2$O—, where at least one of $Z^{11}$, $Z^{12}$ and $Z^{13}$ is —CF$_2$O—;
m, n and p are, independently of one another, 0 or 1;
q and w are, independently of one another, 0, 1, 2, 3 or 4; and
$R^{11}$ is H, F, Cl, OCF$_3$, OCHF$_2$ or CF$_3$.

2. An aldehyde according to claim 1, wherein
$A^{14}$ is

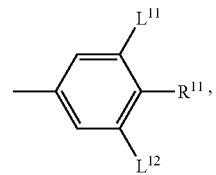

$R^{11}$ is as defined in claim 1, and $L^{11}$ and $L^{12}$, independently of one another, are H or F.

3. An aldehyde according to claim 1, wherein
$Z^{12}$ and $Z^{13}$, independently of one another, are a single bond, —CH$_2$CH$_2$—, —CF$_2$CH$_2$—, —CH$_2$CF$_2$—, —CF$_2$CF$_2$— or —CF$_2$O—.

4. An aldehyde according to claim 1, wherein m is 0.

5. An aldehyde according to claim 1, wherein n and p are 0.

6. An aldehyde, which is a compound of one of the following formulae:

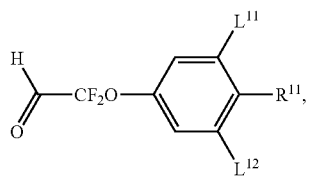
I-A

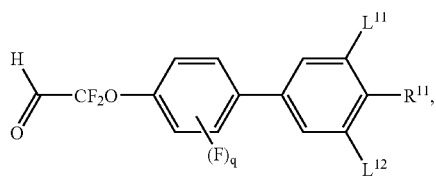
I-B

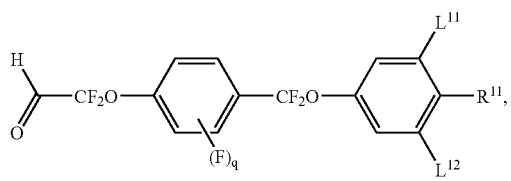
I-C

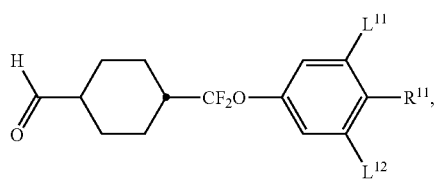
I-D

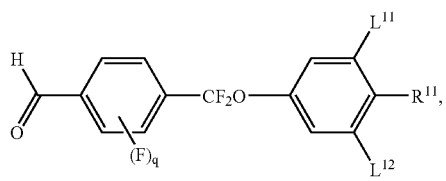
I-E

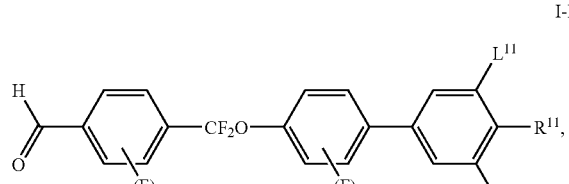
I-F

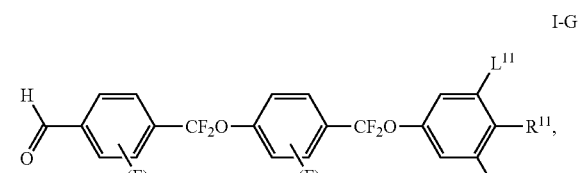
I-G or

-continued

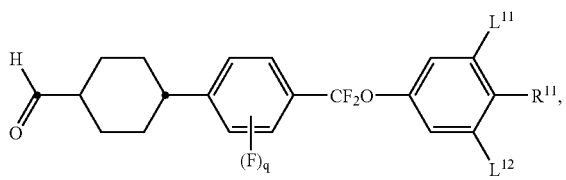
I-H wherein
$R^{11}$ is H, F, Cl, $OCF_3$, $OCHF_2$ or $CF_3$,
$L^{11}$ and $L^{12}$ are, independently of one another, are H or F,
q is 0, 1, 2, 3 or 4, and
q1 and q2, independently of one another, are 0, 1, 2, 3 or 4.

7. A process for preparing a 1,3-dioxane compound, comprising reacting an aldehyde according to claim 1 with a 1,3-diol or a 1,3-bis-silylated derivative of the 1,3-diol.

8. A process according to claim 7, wherein
the 1,3-diol or the 1,3-bissilylated derivative of the 1,3-diol is a compound of formula II:

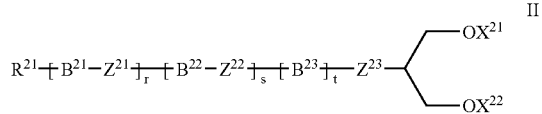
II wherein
r, s and t, independently of one another, are 0 or 1;
$R^{21}$ is an alkyl radical having 1 to 15 carbon atoms which is unsubstituted or mono- or polysubstituted by F, Cl, Br, I and/or —CN, wherein one or more $CH_2$ groups are, independently of one another, replaced by —C≡C—, —CH=CH—, —O—, —S—, —CO—, —CO—O— or —O—CO— in such a way that hetero atoms are not linked directly to one another;
$B^{21}$, $B^{22}$ and $B^{23}$, independently of one another, are

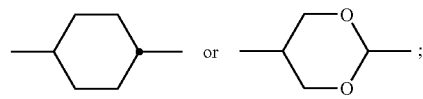

$Z^{21}$, $Z^{22}$ and $Z^{23}$, independently of one another, are a single bond, —$CH_2CH_2$—, —$CF_2CH_2$—, —$CH_2CF_2$—, —$CF_2CF_2$—, —CH=CH— or —C≡C—;
$X^{21}$ and $X^{22}$ are H or $SiR^{22}R^{23}R^{24}$, and
$R^{22}$, $R^{23}$ and $R^{24}$ are each, independently of one another, an alkanyl radical having 1 to 6 carbon atoms, and one or two of the radicals $R^{22}$, $R^{23}$ and $R^{24}$ are optionally phenyl.

9. A process according to claim 7, wherein the aldehyde has a structure of formula Ia:

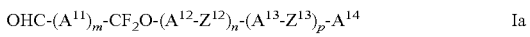
Ia wherein m is 0, and $A^{12}$, $A^{13}$, $A^{14}$, $Z^{12}$, $Z^{13}$, n and p are as defined in claim 7.

10. A process according to claim 7, wherein the aldehyde has a structure of formula Ia:

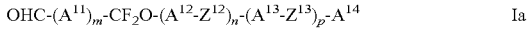
Ia wherein m is 1, $A^{11}$ is 1,4-cyclohexylene, and $A^{12}$, $A^{13}$, $A^{14}$, $Z^{12}$, $Z^{13}$, n and p are as defined in claim 7.

11. An aldehyde according to claim 3, wherein $Z^{12}$ and $Z^{13}$ are, independently of one another, a single bond or —$CF_2O$—.

12. An aldehyde of formula I $$\text{OHC-}(A^{11})_m\text{-}Z^{11}\text{-}(A^{11}\text{-}Z^{12})_n\text{-}(A^{13}\text{-}Z^{13})_p\text{-}A^{14} \qquad \text{I}$$

wherein $A^{11}$ is

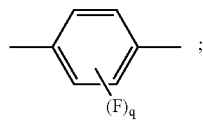

$A^{12}$ and $A^{13}$ are, independently of one another,

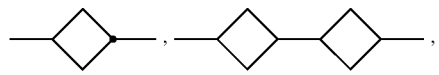

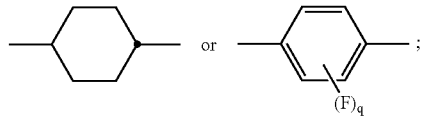

$A^{14}$ is

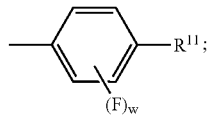

$Z^{11}$ is —$CF_2O$—;
$Z^{12}$ and $Z^{13}$ are, independently of one another, a single bond, —$CH_2CH_2$—, —$CF_2CH_2$—, —$CH_2CF_2$—, —$CF_2CF_2$—, —CH=CH—, —C≡C—, —CO—O—, —O—CO—, —$CH_2O$—, —$OCH_2$— or —$CF_2O$—, where at least one of $Z^{11}$, $Z^{12}$ and $Z^{13}$ is —$CF_2O$—;
m, n and p are, independently of one another, 0 or 1;
q and w are, independently of one another, 0, 1, 2, 3 or 4; and
$R^{11}$ is H, F, Cl, Br, I, CN, or —NCS.

* * * * *

UNITED STATES PATENT AND TRADEMARK OFFICE
CERTIFICATE OF CORRECTION

PATENT NO. : 7,109,381 B2
APPLICATION NO. : 10/854676
DATED : September 19, 2006
INVENTOR(S) : Eike Poetsch et al.

It is certified that error appears in the above-identified patent and that said Letters Patent is hereby corrected as shown below:

Column 28, line 9, in formula I, reads "$(A^{11}-Z^{12})$" should read -- $(A^{12}-Z^{12})$ --

Column 28, line 24 reads " 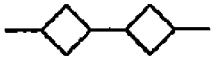 " should read --  --

Column 31, line 9, in formula I, reads "$(A^{11}-Z^{12})$" should read -- $(A^{12}-Z^{12})$ --

Column 31, line 26 reads " 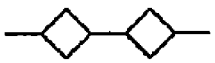 " should read --  --

Signed and Sealed this

Thirteenth Day of March, 2007

JON W. DUDAS
*Director of the United States Patent and Trademark Office*